US00PP10403P

United States Patent [19]

Jessel, Jr.

[11] Patent Number: Plant 10,403

[45] Date of Patent: May 19, 1998

[54] CARNATION PLANT NAMED 'CFPC DELICADO'

[75] Inventor: Walter H. Jessel, Jr., Gonzales, Calif.

[73] Assignee: California Florida Plant Co., L.P., Salinas, Calif.

[21] Appl. No.: 711,032

[22] Filed: Sep. 10, 1996

[51] Int. Cl.[6] ..... A01H 5/00

[52] U.S. Cl. ..... Plt./70.2

[58] Field of Search ..... Plt./70.2

*Primary Examiner*—Howard J. Locker

*Attorney, Agent, or Firm*—Christie, Parker & Hale, LLP

[57] ABSTRACT

A new variety of carnation plant producing light orange flowers.

1 Drawing Sheet

SUMMARY OF THE INVENTION

The present invention relates to a new and distinct variety of carnation plant which was originated by crossing as female parent the variety known as 'CFPC Sunset' (U.S. Plant Pat. No. 7,855) and as male parent an undistributed, unpatented seedling identified as 920205. The varietal denomination of this new carnation is 'CFPC Delicado'.

Among the novel combination of characteristics possessed by the new variety which distinguishes it are very good Fusarium sp. tolerance and medium, sprays of light orange flowers with red markings.

Asexual reproduction by propagation by side shoot cuttings of the new variety as performed in Salinas, Calif., shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety depicted in color as nearly true as it is reasonably possible to make the same in color illustration of this character.

DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart. Phenotypic expression may vary depending upon varying environmental, seasonal and cultural conditions.

The information provided herein is based on observations of plants grown inside commercial greenhouses at Salinas, Calif. The height of plant and flower and foliage size are established as an average using standard commercial cultural practices. Where terms such as average, normal, ordinary, etc., are used, the characteristics so described are not considered distinguishing.

Name: 'CFPC Delicado'.

Classification:

*Botanical.*—*Dianthus caryophyllus.*

*Commercial.*—Carnation, spray-type.

Parentage:

*Female parent.*—'CFPC Sunset'.

*Male parent.*—920205.

1. Plant:

*Height.*—About 39 inches (first flowering).

*Growing habit.*—Herbaceous, semi-upright.

*Blooming habit.*—As a spray.

*Blooming season.*—Year round.

*Rooting time.*—About 18–20 days.

*Mutation prone.*—No.

*Disease resistance.*—Very good.

*Temperature tolerance.*—Wide range.

*Breaking action.*—Very good, about 8 to 9 lateral shoots per plant.

2. Foliage:

*Color.*—Upper side: Near 137B. Lower side: Near 137A.

*Size.*—About 5¾ inches long, about ⅞ inches wide.

*Quantity.*—Numerous.

*Shape.*—Lanceolate.

*Texture.*—Smooth.

*Ribs.*—Central, keeled.

*Arrangement.*—Bi-lateral along stem.

*Stem color.*—Near 137A.

3. Bud:

*Shape.*—Ovoid.

*Color.*—Near 138A.

*Length.*—About 1⅛ inches.

*Diameter.*—About ½ inch.

4. Calyx:

*Number of sepals.*—About 6.

*Length.*—About ⅞ inch.

*Width.*—About ¼ inch.

*Color.*—Outside— Near 144A. Inside— Near 145A.

5. Bloom:

*Shape.*—Round.

*Size.*—Diameter average: About 2½ inches. Depth average: About ¾ inches.

*Borne.*—Terminal as a spray, approximately 10 open flowers and buds per spray, stem length approximately 39 inches.

*Color.*—General tonality: Light orange, very slight picotee red. Upper side: Near 27A, lightens to near 27B toward extremities and in the petals at center; picotee edge is near 44B on the tops. Lower side: Near 27B, picotee edge near 44C (on reverse). Center: Near 27B. Outer petals: Near 27B with near 44B.

*Keeping quality.*—Good, petals dry up after about 2 to 3 weeks and remain attached.

*Fragrance.*—Very slight.

6. Petals:

*Number.*—About 32.

*Outer petals.*—Length; About 1 ¾ inches. Width: About 1 inch.

*Central petals.*—Length: About 1½ inches. Width: About ½ inch.
*Texture.*—Smooth.
*Form.*—Fan shaped.
*Appearance.*—Shiny, petal margins finely serrated.

7. Reproductive organs:
*Stamens.*—About 5.
*Anthers.*—About 1/16 inch, near 19B.
*Filaments.*—About 1 inch, near 157C.
*Pistil.*—Number: About 1. Color: White. Length: About 1 inch.
*Stigma.*—Number: About 2. Color: Whiter than 155D.
*Ovary.*—Shape: Conical. Color: Base— Near 157D. Body— Near 157D. Apex— 141D.
*Fertility.*—Female: Average. Male: Average.

I claim:

1. A new and distinct variety of carnation plant substantially as shown and described.

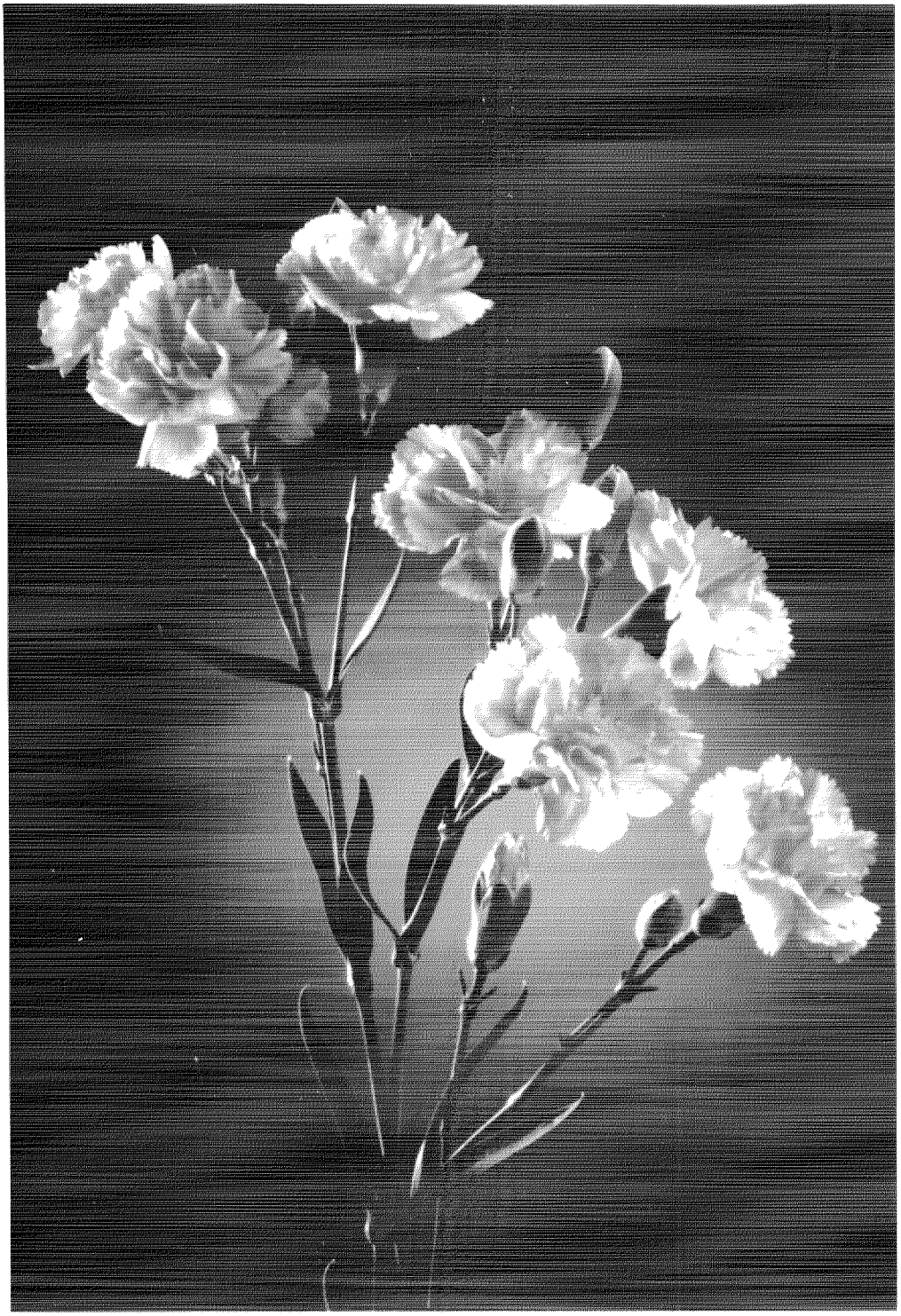

* * * * *